United States Patent [19]

Spanier et al.

[11] Patent Number: 5,166,752
[45] Date of Patent: Nov. 24, 1992

[54] SIMULTANEOUS MULTIPLE ANGLE/MULTIPLE WAVELENGTH ELLIPSOMETER AND METHOD

[75] Inventors: Richard F. Spanier, Chester; Robert G. Wolf, Succasunna; Robert M. Loiterman; Mitchell E. Haller, both of Hackettstown, all of N.J.

[73] Assignee: Rudolph Research Corporation, Flanders, N.J.

[21] Appl. No.: 640,100

[22] Filed: Jan. 11, 1990

[51] Int. Cl.[5] .............................................. G01J 4/00
[52] U.S. Cl. ................................... 356/369; 356/367; 250/201.2
[58] Field of Search ................ 356/364, 366, 367, 369; 250/201.2, 201.6, 225

[56] References Cited

U.S. PATENT DOCUMENTS

| | | | |
|---|---|---|---|
| 4,030,836 | 6/1977 | Smith | 250/225 |
| 4,052,666 | 10/1977 | Fletcher et al. | 324/58.5 B |
| 4,053,232 | 10/1977 | Dill et al. | 290/225 |
| 4,077,720 | 3/1978 | Kasai | 356/369 |
| 4,434,025 | 2/1984 | Robillard | 156/601 |
| 4,472,633 | 9/1984 | Motooka | 250/338 |
| 4,516,855 | 5/1985 | Korth | 356/367 |
| 4,585,348 | 4/1984 | Chastang et al. | 356/369 |
| 4,647,207 | 3/1987 | Bjork et al. | 356/369 |
| 4,653,924 | 3/1987 | Itonaga et al. | 356/369 |
| 4,655,595 | 4/1987 | Bjork et al. | 356/369 |
| 4,672,196 | 6/1987 | Canino | 250/225 |
| 4,686,360 | 8/1987 | Gorgon | 250/201.2 |
| 4,725,145 | 2/1988 | Azzam | 356/367 |
| 4,834,539 | 5/1989 | LeBris et al. | 356/369 |
| 4,837,603 | 6/1989 | Hayashi | 356/369 |
| 4,838,695 | 6/1989 | Mansuripur et al. | 356/369 |
| 4,850,711 | 7/1989 | Sano et al. | 356/369 |
| 4,866,264 | 9/1989 | Biricik et al. | 250/225 |
| 4,957,368 | 9/1990 | Smith | 356/369 |
| 4,999,014 | 3/1991 | Gold et al. | 356/369 |

FOREIGN PATENT DOCUMENTS 1125676 3/1962 Fed. Rep. of Germany ...... 356/367

Primary Examiner—Richard A. Rosenberger
Attorney, Agent, or Firm—Antonelli, Terry, Stout & Kraus

[57] ABSTRACT

The ellipsometer and method involve directing polarized light for interaction with an optical system under study at different angles of incidence from a single beam of light and detecting the light interacted with the optical system by reflection and/or transmission for each of a plurality of different angles of incidence. The simultaneous illumination of the optical system under study at a whole range of angles of incidence from a single beam of light and the collection a large multiplicity of data from the different angles detected can be accomplished rapidly and easily and with accuracy without scanning and with only one ellipsometer. A lens is used to focus the incoming light to provide the range of different angles of incidence. The range of angles is at least one or two degrees and preferably thirty degrees or more. A second lens refocuses the interacted light to a linear, multi-element detector array which extends in the plane of the incidence. Each of the detector elements detects a narrow range of angles of incidence within the relatively wider range of angles of incidence of the illuminating beam. If the incident illuminating rays are polychromatic and a wavelength dispersing element acts on the reflected rays each detector element of a square array detects a narrow range of wavelengths and angles of incidence.

42 Claims, 8 Drawing Sheets

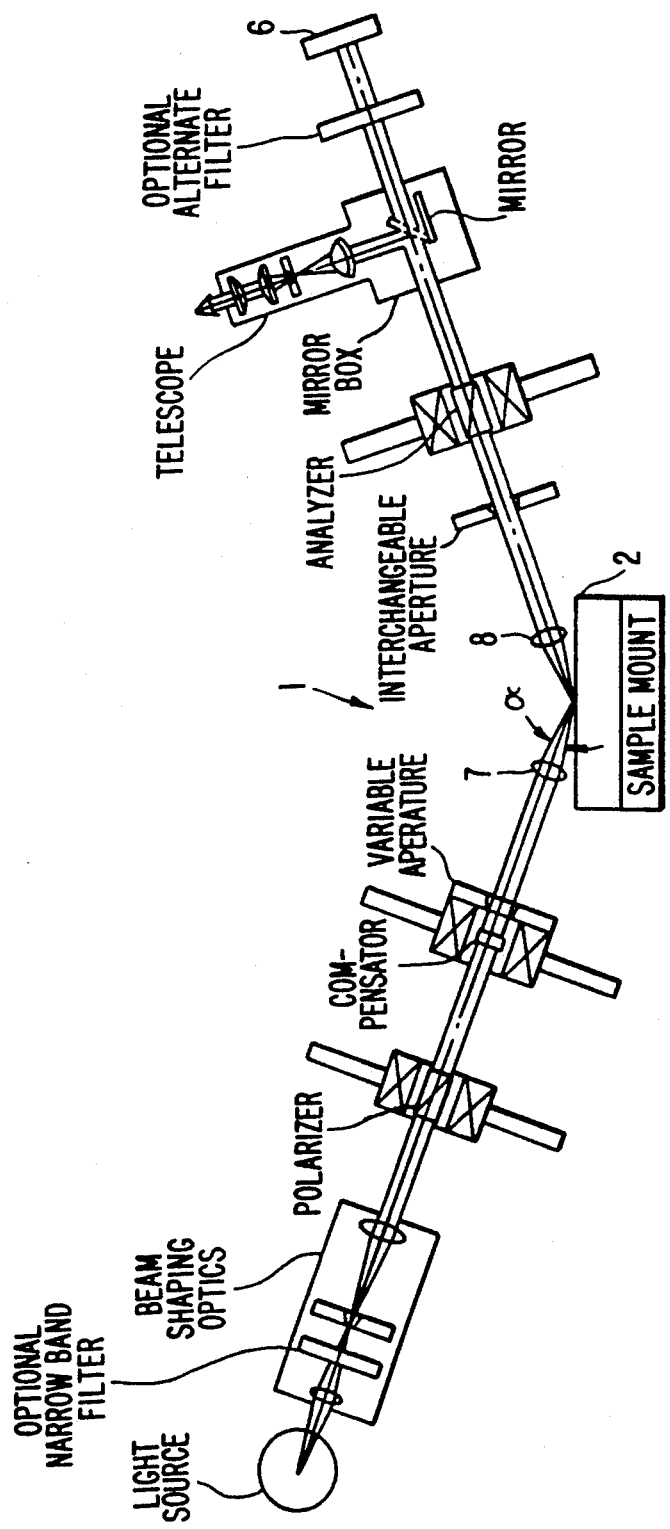

SIMULTANEOUS MULTIPLE ANGLE/MULTIPLE WAVELENGTH ELLIPSOMETER AND METHOD

TECHNICAL FIELD

The present invention relates to an ellipsometer and an ellipsometry method for measuring the change in polarization state of light upon interaction with a sample for determining characteristics of the sample.

BACKGROUND ART

Ellipsometry, as defined by R. A. Azzam and N. M. Bashara in *Ellipsometry and Polarized Light*, published by North-Holland Physics Publishing, 1987 edition, is an optical technique for the characterization and observation of events at an interface or film between two media and is based on exploiting the polarization transformation that occurs as a beam of polarized light is reflected from or transmitted through the interface or film. Two factors make ellipsometry particularly attractive: (1) its essential non-perturbing character (when the wavelength and intensity of the light beam are properly chosen) hence its suitability for in-situ measurements, and (2) its remarkable sensitivity to minute interfacial effects, such as the formation of a sparsely distributed sub-monolayer of atoms or molecules. The great diversity of situations in nature and man-made systems where interfaces and films play an important role has lead to the application of ellipsometry in a wide spectrum of fields such as physics, chemistry, materials and photographic science, biology, as well as optical, electronic, mechanical, metallurgical and biomedical engineering.

Ellipsometry is sometimes referred to as polarimetry, generalized polarimetry, or complete polarimetry. The latter names are more common especially when interaction with the sample involves transmission of light through the bulk of the sample and the polarization transformation depends on bulk sample properties as well as surface properties and films.

Azzam and Bashara further state in their aforementioned book that ellipsometry can be generally defined as the measurement of the state of polarization of a polarized vector wave. Ellipsometry is generally conducted in order to obtain "information" about an "optical system" that modifies the state of polarization. In a general scheme of ellipsometry, a polarized light-wave is allowed to interact with an optical system under investigation. The interaction changes the state of polarization of the wave. Measurement of the initial and final states of polarization, repeated for an adequate number of different initial states, leads to the determination of the law of transformation of polarization by the system as described, for example, by its Jones or Mueller matrix. To extract more fundamental information about the optical system than is conveyed by its Jones or Mueller matrix, it is necessary to examine light-matter interaction within the system by the electromagnetic theory of light. In other words, it is necessary to study the details of the internal polarization-modifying processes that are responsible for the external behavior as described by the measured Jones or Mueller matrix of the system.

An operational diagram of a general ellipsometer arrangement as shown in *Ellipsometry and Polarized Light* is shown in FIG. 1 of the drawings. A beam from a suitable light source (L) is passed through a variable polarizer (P) to produce light of known polarization. This light interacts with the optical system (S) under study and its polarization is modified. The modified state of polarization at the output of the system is measured (analyzed) by a polarization analyzer (A) followed by a photodetector (D). If the light interaction with the sample under study varies with wavelength, a monochromatic light source must be used or a means of isolating quasimonochromatic portions (with known wavelengths) of the light must be provided.

One way in which the light wave can interact with the optical system is by being reflected from a surface of the optical system (S). This reflection causes the state of polarization to be changed abruptly. Such a change can be explained using the Fresnel reflection coefficients for the two linear polarizations parallel (p) and perpendicular (s) to the plane of incidence. Another way the light wave can interact with the optical system is transmission through the material of the optical system. When the polarization state change depends on the angle of interaction of the light beam and the sample under study, as for example with reflection from (or oblique transmission through) a sample, the incident light should be as collimated as possible so only a single angle of incidence is measured at one time.

Azzam and Bashara explain that, since the time of Drude, reflection ellipsometry has been recognized as an important tool for the study of surfaces and thin films. Among the many useful applications of ellipsometry are: (1) measurement of the optical properties of materials and their frequency dependence (wavelength dispersion), the materials may be in the liquid or solid phase, may be optically isotropic or anisotropic, and can be either in bulk or thin-film form; (2) monitoring of phenomena on surfaces that involve either the growth of thin films starting from a submonolayer (e.g., by oxidation, deposition, adsorption or diffusion of impurities), or the removal of such films (e.g., by desorption, sputtering or diffusion); and (3) measurement of physical factors that affect the optical properties such as electric and magnetic fields, stress or temperature.

A description of the principles of ellipsometry, and a discussion of the reflection process, the measurement process, and data reduction can be found in "Ellipsometry A Century Old New Technique" by Dr. Richard F. Spanier, *Industrial Research*, September 1975, which article is incorporated herein by reference. A diagram of a conventional ellipsometer from Dr. Spanier's article is shown in FIG. 2B. Many additional types of automated and manually operated ellipsometers are known in the art. Dr. Spanier states in the article that ellipsometry involves the measurement of tan $\psi$, the change in the amplitude ratio upon reflection, and $\Delta$, the change in the phase difference upon reflection. The quantities $\Delta$ and $\psi$ are functions of the optical constants of the surface, the wavelength of the light used, the angle of incidence, the optical constants of the ambient medium, and for film-covered surfaces, the thicknesses and optical constants of the films.

Thus, in order to be able to compute the information about a sample's properties which cause a polarization state change in the reflected light, it is necessary to convert the polarization state change together with the angle of incidence and wavelength into physical properties of the sample according to some mathematical model. Properties such as refractive index, thickness, and absorption index of films on a surface or the optical constants of bare surfaces can be computed, for example. Similarly, in the case of transmitted light, properties such as the birefringence of the bulk material can be computed. Each ellipsometric measurement of polarization state change yields one value for Δ and one value for ψ. Thus, at best, two of the properties of the surface (whether or not film covered) or two properties of the bulk (in the case of transmitted light) can be computed if values for the remaining properties are known from other sources.

Frequently, in the art, one can compute more of these properties, of film covered surfaces, for example, if one has values for Δ and values for ψ, at more than one angle of incidence; preferably, at many angles of incidence. Theoretically, one property can be computed for each independent Δ and one property can be computed for each independent ψ measured but it is better to overdetermine the unknowns with extra values of Δ and ψ. Accordingly, it is advantageous to measure as many angles of incidence on a particular sample as possible. However, this has not been done frequently in the past because it is so cumbersome to get the data by making separate successive measurements at each angle through the use of a scanning technique.

It has also been proposed to provide ellipsometers with a plurality of duplicate setups with multiple beams all of different, discrete angles in order to simultaneously obtain information for light at different angles of incidence. These ellipsometers essentially combine several ellipsometers of the known type and use them simultaneously. This technique is limited in the number of angles that can be simultaneously measured because of the need for a plurality of ellipsometers, which can add considerably to the initial cost and maintenance of such a system.

The following U.S. patents are cited of interest for their disclosures relating to ellipsometry and ellipsometers.

| | |
|---|---|
| 4,030,836 | 4,077,720 |
| 4,052,666 | 4,434,025 |
| 4,053,232 | 4,472,633 |
| 4,516,855 | 4,725,145 |
| 4,585,348 | 4,834,539 |
| 4,647,207 | 4,837,603 |
| 4,653,924 | 4,850,711 |
| 4,655,595 | 4,866,264 |

DISCLOSURE OF INVENTION

There is a need in the art for an improved ellipsometry method and ellipsometer for measuring a large plurality of angles of incidence at one time, quickly and without complicated operator intervention or scanning and wherein only one ellipsometer and a single beam are required. The aim of the present invention is to provide such an improved ellipsometry method and ellipsometer and to thereby overcome the aforementioned disadvantages of the conventional methods and ellipsometers.

More particularly, an object of the invention is to provide an improved ellipsometry method and ellipsometer which permit the simultaneous illumination of a sample at a whole range of angles of incidence from a single beam of light and which permit the rapid, easy collection of a large multiplicity of data for different angles or ranges of angles within the whole range of angles.

A further object of the invention is to provide an improved ellipsometry method and ellipsometer as described in the previous paragraph which permits easy collection of a large multiplicity of data at different light wavelengths as well as angles.

An additional object of the invention is to provide an improved ellipsometry method and ellipsometer having the aforementioned advantages wherein the actual illuminated spot on the sample area can be extremely small so that all the rays with different angles of incidence measure essentially the same region of the sample.

These and other objects of the invention are attained by the ellipsometry method of the invention which comprises directing polarized light onto an optical system under study, such as a surface, and analyzing the polarization state of light interacted with the surface, namely analyzing light reflected from the surface and/or light transmitted through the surface and bulk material, for example, wherein polarized light from a single beam of light is simultaneously directed onto the optical system under study at different angles of incidence. Conventional ellipsometers are built to illuminate a sample with a beam of light that is as parallel as possible within the design constraints of the ellipsometer, e.g. with all rays striking the sample at nearly the same angle. However, applicants have found that by delivering polarized light to the sample at a multiplicity of angles from a single beam of light and through the use of a plurality of light detector means for detecting the light reflected from the surface (or transmitted through the surface and bulk material) for each of a plurality of different angles of incidence, data can be rapidly generated in terms of Δ and ψ for each of the plurality of different angles of incidence for which reflected or transmitted light is separately detected by respective ones of a plurality of light detector means.

In the disclosed embodiment the light at different angles of incidence is provided by directing parallel light through one or more lenses for focusing the light on the surface. The lens has an effective aperture to focal length ratio for focusing the light on the surface at angles of incidence which vary over a range. Although a range of angles of as low as 1 to 2 degrees may be useful for some samples, a range of angles of incidence of from 2° to more than 30° is preferred. The larger the range of angles of incidence the better the utility and versatility of the equipment. The light directed onto the surface at different angles of incidence is most generally elliptically polarized light. In one form of the invention the light is monochromatic light but according to another form of the invention the polarized light could be polychromatic light provided a wavelength isolation means, such as a filter, monochromator or spectrometer is present to assure that the detectors see only a quasimonochromatic portion thereof during one measurement of Δ, and ψ. In yet another form of the invention, the polarized light can be derived from two or more light sources (that may be monochromatic or polychromatic) arranged to direct the light along a common optical axis, wherein light from any single one of the sources can be selected by only energizing the correct source, or selected with a movable mirror, or selected by blocking the remainder with shutters, filters, monochromators, or selected by a combination of them. The polarized light is simultaneously directed at different angles of incidence onto the same spot on the surface of the sample. In the illustrated embodiment, the spot has a diameter of 10 microns.

The step of detecting the light reflected from the surface or transmitted through the sample for each of a plurality of different angles of incidence according to the ellipsometry method of the invention involves the use of an array of light detector means which are placed to intercept and detect the light reflected at a plurality of angles or transmitted along a plurality of angles. The array is a linear array in one form of the invention. Each of the plurality of different angles of incident light is separately detected simultaneously by respective ones of the plurality of light detector means. In one embodiment, the detected light is refocused by passing it through one or more lenses and the polarization state analyzer before it is detected. In other embodiments the lenses are not necessary.

The method of the invention can also further include the step of dispersing light (as a function of wavelength) reflected from the surface (or transmitted through the material) and detecting wavelength variation of the reflected (transmitted) dispersed light as, for example, through the use of an additional array of light detector means extending transverse to the plane of incidence of the central ray of the polarized light. This method permits simultaneous detection of both wavelength variation and angle of incidence variation.

The ellipsometer according to the invention comprises means for directing polarized light so that it interacts with an optical system under study, means for analyzing the polarization state of the light interacted with the optical system under study as by reflection from and/or transmission through the optical system, and wherein the means for directing polarized light includes means for simultaneously directing polarized light from a single beam of light onto the optical system under study at different angles of incidence. The disclosed forms of the invention involve directing polarized light onto the optical system on a single spot with a cone of polarized light which is derived from passing a single beam through a lens or lenses for focusing the light on the optical system. The lens has an effective aperture to focal length ratio for focusing the light on the surface with angles of incidence which vary over a range of at least one or two degrees. Preferably, the range of angles of incidence is equal to or greater than 30 degrees as noted above.

The linear array of detectors of the ellipsometer, which are located in the plane of incidence of the central ray of the polarized light for detecting reflected or transmitted light, are preferably solid state photosensitive detectors which are integrated on a semiconductor chip. Particularly, the photosensitive detectors are photodiodes which each function as a separate detector for detecting a narrow range of angles of incidence of the rays illuminating the sample. Alternatively completely separate detectors or photomultipliers could be used and/or scanning techniques could be employed during detection.

These and other objects, features and advantages of the present invention will become more apparent from the following description when taken in connection with the accompanying which show, for purposes of illustration only, several embodiments in accordance with the present invention.

BRIEF DESCRIPTION OF DRAWINGS

FIG. 3A is a schematic illustration of an ellipsometer according to a first embodiment of the invention.

BEST MODE FOR CARRYING OUT THE INVENTION

Figure 1:
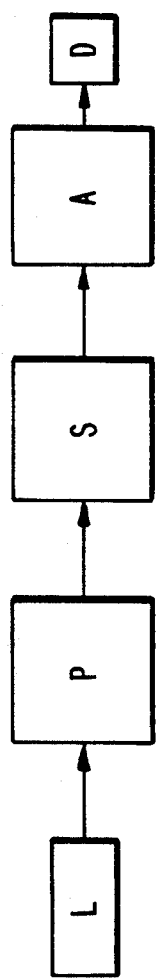
FIG. 1 is an operational diagram of a general ellipsometer or arrangement wherein L, P, S, A, and D represent a light source, controlled polarizer, optical system under measurement, variable polarization analyzer, and photodetector, respectively.
Figure 2A:
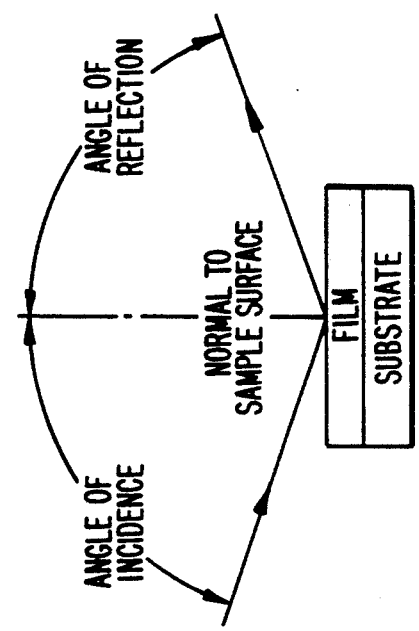
FIG. 2A is a schematic diagram illustrating a known reflection ellipsometry arrangement wherein the incoming collimated polarized light is reflected at an angle equal to its angle of incidence.
Figure 2B:
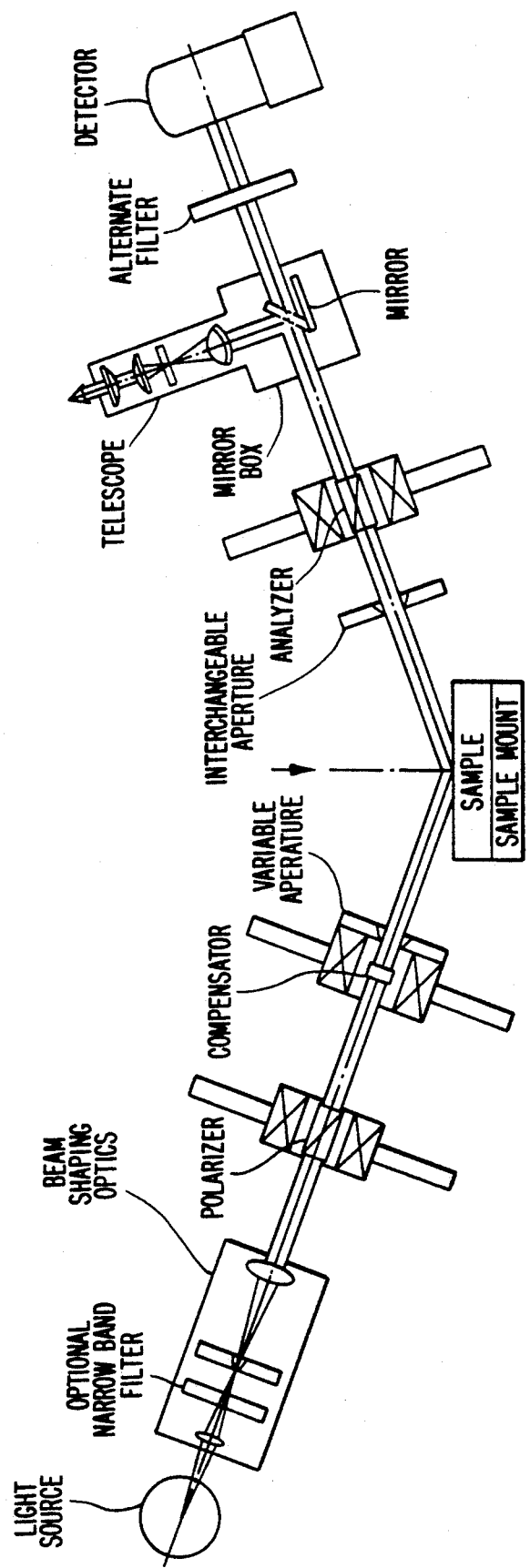
FIG. 2B is a schematic diagram of a conventional nulling or photometric ellipsometer which measures changes in the state of polarized light reflected at a single angle incidence from the surfaces of samples resting on a sample mount.

The ellipsometer 1 of the invention as shown in FIG. 3A comprises means for directing polarized light onto the surface 2 and means for analyzing the polarization state of the light reflected from the surface. The means for directing includes a light source, beam shaping optics with an optional optical narrow band filter, a polarizer, a compensator and a variable aperture as in the conventional ellipsometer of FIG. 2B. In addition, the means for directing further includes means for simultaneously directing polarized light from a single beam of light from the light source onto the surface 2 at different angles of incidence. This means for simultaneously directing the light at different angles of incidence onto the surface 2 comprises a focusing lens system 7. The lens system 7 has an effective aperture to focal length ratio for focusing the light on the surface 2 with angles of incidence which vary over a range of angles of at least one or two degrees. More particularly, in the illustrated preferred embodiment the range of angles of incidence α is 30 degrees. Larger angles could be employed for directing rays at the sample 2.

The focusing lens system 7 focuses the polarized light which may be from a He-Ne laser for example, down to a single small spot or point on the surface 2. The schematic illustration of FIG. 4A depicts several rays A, B, C and D having widely varying angles of incidence which are focused on a single, small spot on the surface 2. Thus, the light directed on the small spot on surface 2 contains rays at many angles of incidence above and below the angle of incidence of the central ray through the focusing lens. Each one of the incoming rays is reflected at an angle equal to its angle of incidence with the polarization state of each of the rays being altered by that reflection, see rays A', B', C' and D' in FIG. 4A. A detector array 6 is employed to detect a plurality of rays reflected from the surface 2 individually over different, narrow ranges of angles of incidence to simply and quickly obtain data at a plurality of angles of incidence. The means for analyzing includes the detector array as well as the analyzer and other elements as shown in FIG. 3A and in some embodiments additional lenses represented by lens 8 in the reflected light.

As shown in FIGS. 3A and 4A the diameter d of the lenses 7 and 8 corresponds to their effective diameter. In the illustrated embodiment the lenses 7 and 8 each have a diameter d of 18 mm and a focal length 1 of 34 mm. Other effective lens diameters and focal lengths could be employed so long as a range of angles of incidence, preferably at least 30°, is provided. The lens diameter and focal length are chosen with a view toward maximizing the number of angles of incidence of the light beams which strike the surface 2. FIG. 4B is similar to FIG. 4A but shows an arrangement where light is transmitted through the sample rather than reflected from a surface of the sample.

The refocusing lens or lenses 8 directs the reflected (transmitted) light toward the detector array 6. However, a refocusing lens need not be employed as the reflected (transmitted) light could be made to directly impinge upon an array of detectors. It is important that the lenses 7 and 8 do not themselves alter the polarization state of the light.

The detector array 6 is a linear, multiple element detector wherein each of the detector elements 9 can detect a narrow range of angles of incidence of the rays that illuminate the sample. In the disclosed embodiment the array 6 is a solid-state photosensitive detector array wherein the separate detector elements 9 are all integrated on one circuit chip. Particularly, the detector elements comprise a linear array of photodiodes. While integrated on a single circuit chip, the individual photodiodes can function as separate detectors. The linear array of the disclosed embodiment comprises 128 detector elements arranged in a row to provide data for 128 different angles of incidence where the full array is illuminated by the reflected (transmitted) light. The number of individual detector elements 9 could be more or less than that in the disclosed embodiment and the detector elements need not be integrated on a single chip but could be discrete detectors. By using a plurality of detector elements, it is possible to simultaneously detect the light reflected from the surface (or transmitted through the sample) for each of a plurality of different angles of incidence. It is also possible with the invention to employ a smaller number of detector elements which could be sequentially moved to mechanically scan the reflected (transmitted) rays for detection but this technique would require more time and could be less accurate, depending upon positioning accuracy.

The physical size of each of the detector elements is less than the expanse of the reflected rays so that each element detects only a certain narrow range of angles of incidence on the illuminating side. The output of each of the detectors is used in a conventional manner as with real time computer techniques to generate data in terms of $\Delta$ and $\psi$ for each of those narrow ranges of angles of incidence. The data is then interpreted in a conventional manner. It matters in general which direction the linear array runs; the linear array preferably runs in the plane of the optical system. In the disclosed embodiment, the long axis of the linear detector array 6 lies in the plane of incidence of the central ray and perpendicular to the central ray for detecting the maximum number of incidence angles.

Figure 3B:
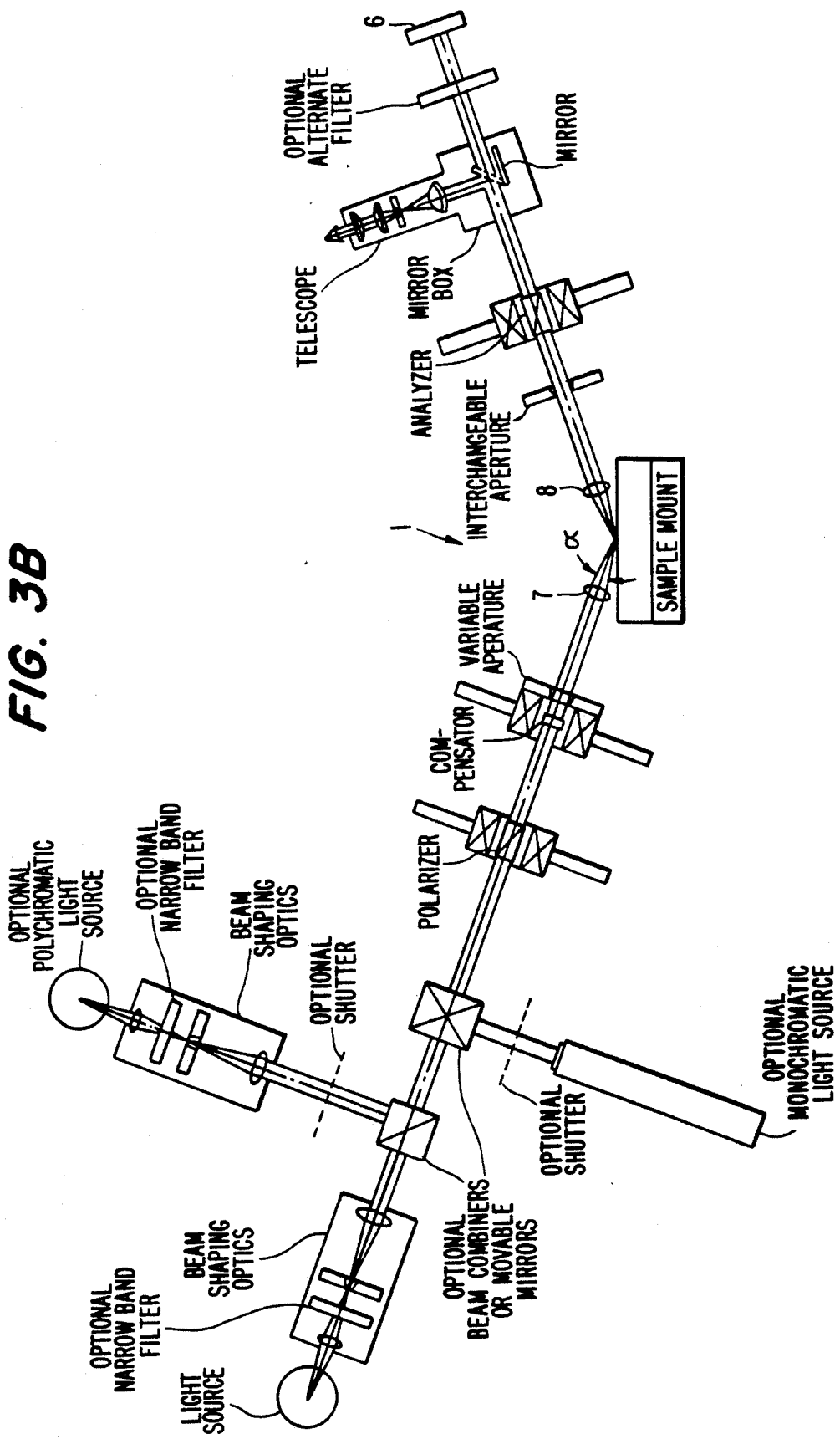
FIG. 3B is similar to 3A but illustrates the use of more than one light source.
Figure 4A:
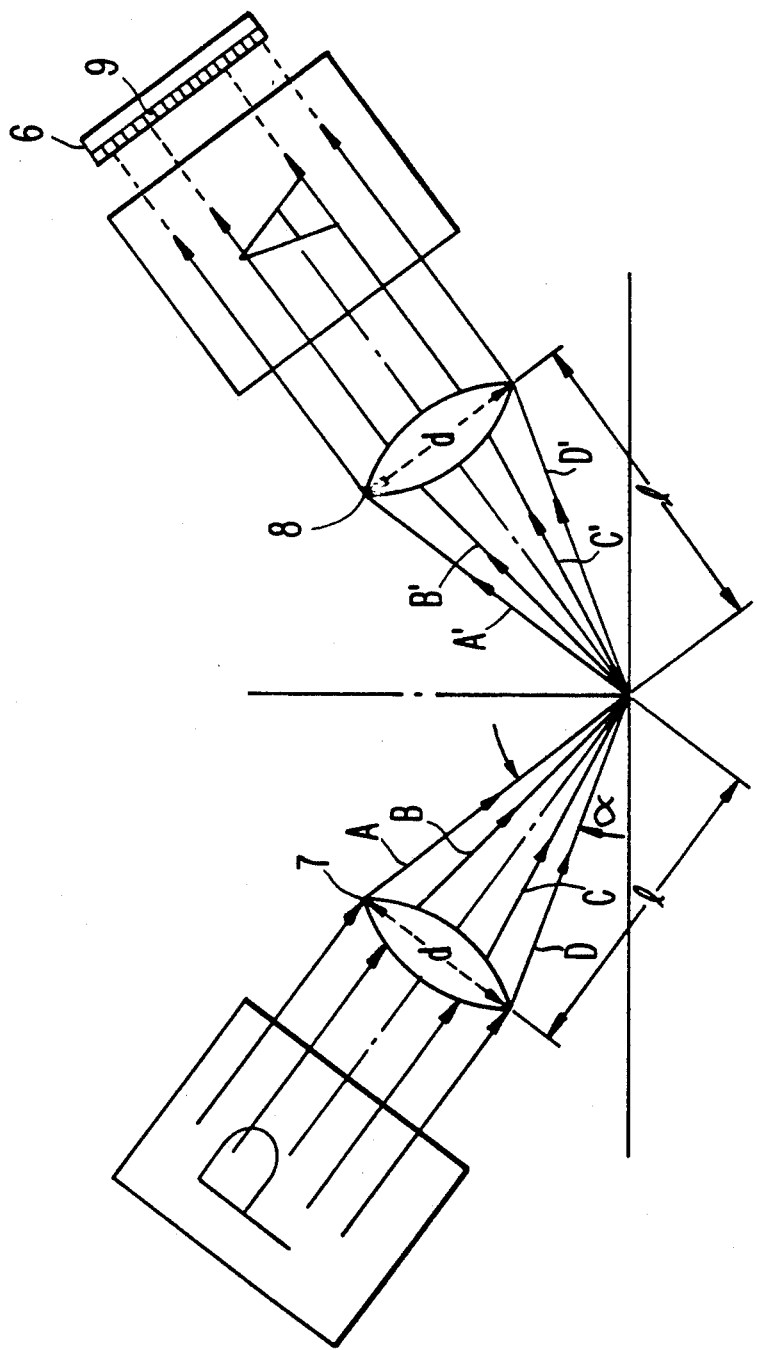
FIG. 4A is a simplified diagram of the ellipsometer of FIG. 3A illustrating a lens system for focusing, a lens system for refocusing reflected light and a linear detector array for detecting the reflected light from the surface for each of a plurality of different angles of incidence.
Figure 5:
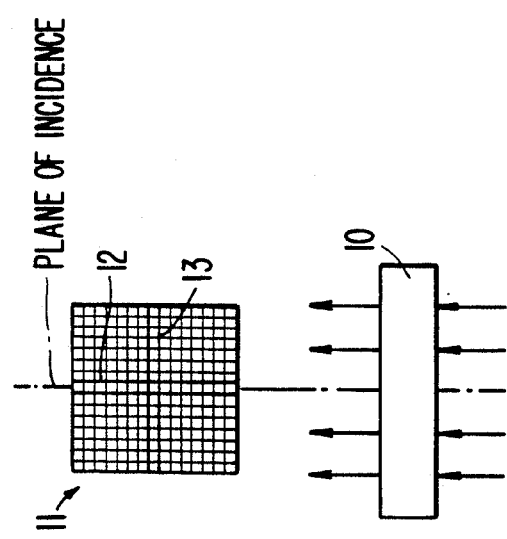
FIG. 5 is a schematic illustration of a portion of an ellipsometer according to a second embodiment of the invention wherein a wavelength dispersing element is provided along with an area array of detectors for detecting angle of incidence variation at a plurality of wavelengths.

The embodiment of the invention shown in FIG. 5 of the drawings is similar to that illustrated in FIGS. 3A and 4A except that polychromatic light is directed toward the sample rather than monochromatic light. In addition, a dispersing element 10 is provided in the reflected (or transmitted) beam for dispersing the reflected (transmitted) light from every angle of incidence. The detector area array 11 comprises columns of detector elements 12 arranged in linear arrays that are parallel to the plane of incidence of the central ray for detecting variations of angle of incidence. Each column of detector elements 12 sees only a quasimonochromatic portion of the polychromatic light for detecting rays reflected (transmitted) from a plurality of angles of incidence. Additionally, rows of detector elements 13 extend transverse to the plane of incidence of the central ray. Each row of detector elements 13 detect the wavelength variation of the dispersed, reflected (transmitted) beam from one of the plurality of angles of incidence. A minimum of one row and one column of detectors are required to detect both angle of incidence and wavelength variation. Additional rows and columns of detectors can provide additional useful information. The ellipsometer of FIG. 5 is advantageous in that it enables simultaneous detection of the beam as a function of angle of incidence and wavelength without scanning either.

From the description of the ellipsometer of the invention, it is apparent that the ellipsometry method of the invention comprises directing polarized light onto a sample surface and analyzing the polarization state of the light reflected from the surface (or transmitted through the sample), wherein polarized light from a single beam of light is simultaneously directed onto the sample at different angles of incidence. In the disclosed forms of the invention, the light is directed onto the sample surface at a single spot with a cone of polarized light derived from the single beam. The angles of incidence preferably vary over a range equal to or greater than 30 degrees but some embodiments may provide as little as 2° of range or a range which is between 2° and 30°. Data is gathered for a plurality of different angles of incidence within the range of angles of incidence by detecting the light reflected from the surface (or transmitted through the sample) for each of a plurality of different angles of incidence.

Ellipsometry, in general, requires an awareness of the angles of incidence of the light striking the sample. Truly, sample alignment, both in tilt and height is important, and alignment telescope microscopes are often provided to aid in sample alignment. With the ellipsometer of the invention, the detector array can be used to not only simultaneously measure the multiple angles of incidence of the single beam, but can also be used to initially detect whether or not the reflecting surface 2 is in the correct plane relative to the instrument. This is accomplished by eliminating rays within a certain area of the sample of the incoming beam and determining which detector element or elements are dark or not illuminated as a result. Based upon this determination, the operator can change the sample plane as by raising the height of the sample mount 5, for example, until the correct pixel (or pixels) is dark.

Figure 6:
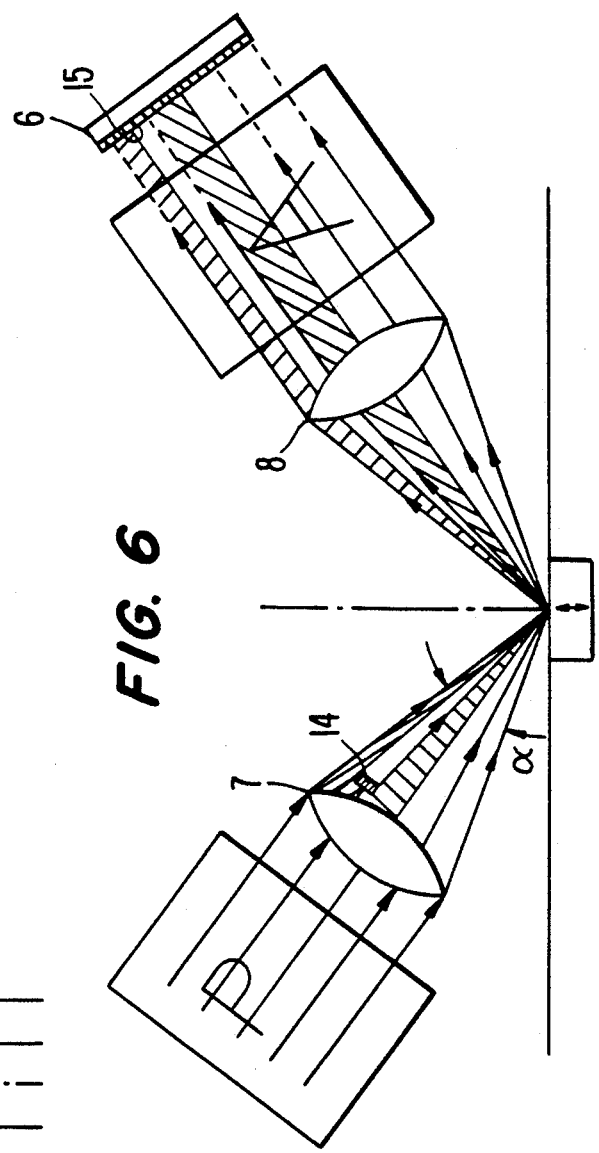
FIG. 6 is a schematic illustration of an ellipsometer of the type shown in FIGS. 3A and 4 where a portion of the incoming rays to the sample are blocked within a certain, known area to darken a portion of the detector array for properly aligning the sample in preparation for performing the ellipsometry method of the invention.

As shown in FIG. 6, a blocking element 14 obstructs the light from the focusing lens 7 in a certain known area thereby creating a darkened area 15 over a portion of the detector array 6. If the appropriate detector elements are not dark, the operator can correct this by raising or lowering the sample mount so that the sample is in the correct plane or elevation. From the above, it can be seen that the ellipsometer and ellipsometry method of the invention permit the simultaneous illumination of a sample at a whole range of angles of incidence from a single beam of light and collection of a large multiplicity of data for different angles of incidence rapidly and easily and with accuracy. The relative angle certainties are more accurate than with conventional mechanical scanning since the relative positions of the detector elements of the detector array are accurately fixed with respect to one another and the ellipsometer during generation of all data. Further, advantageously the actual illuminated spot on the sample area can be extremely small so that all the rays are really measuring nearly the same region of the sample. Therefore, the sample properties can be quickly and accurately computed.

Figure 7A:
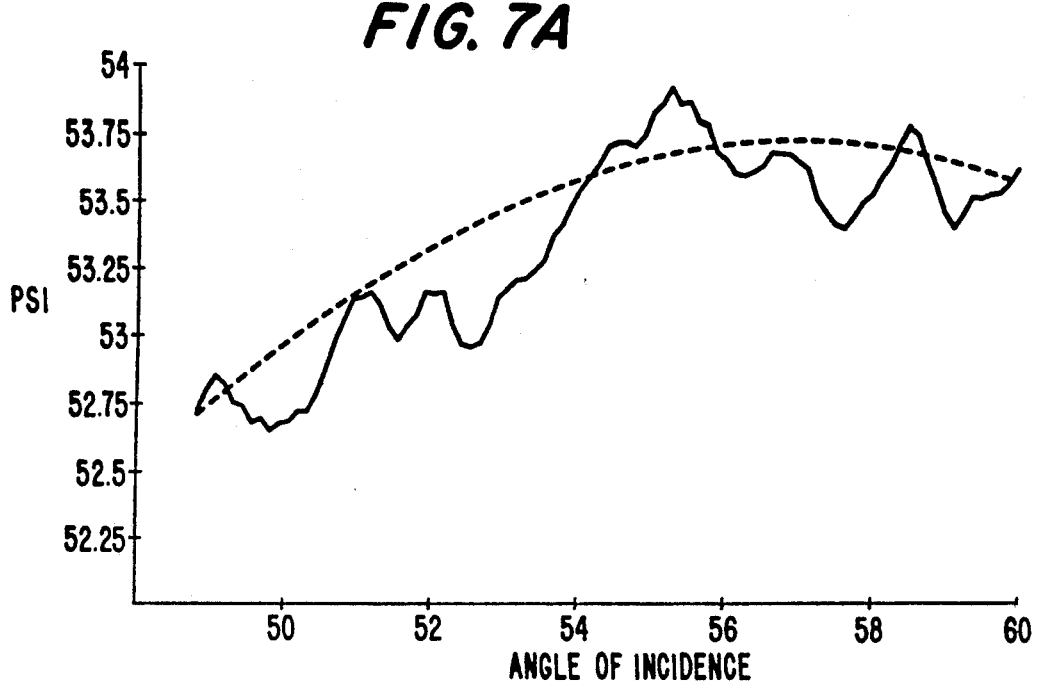
FIG. 7A is a graph of measured values of psi as a function of angle of incidence obtained from a sample using an ellipsometer according to the invention.
Figure 7B:
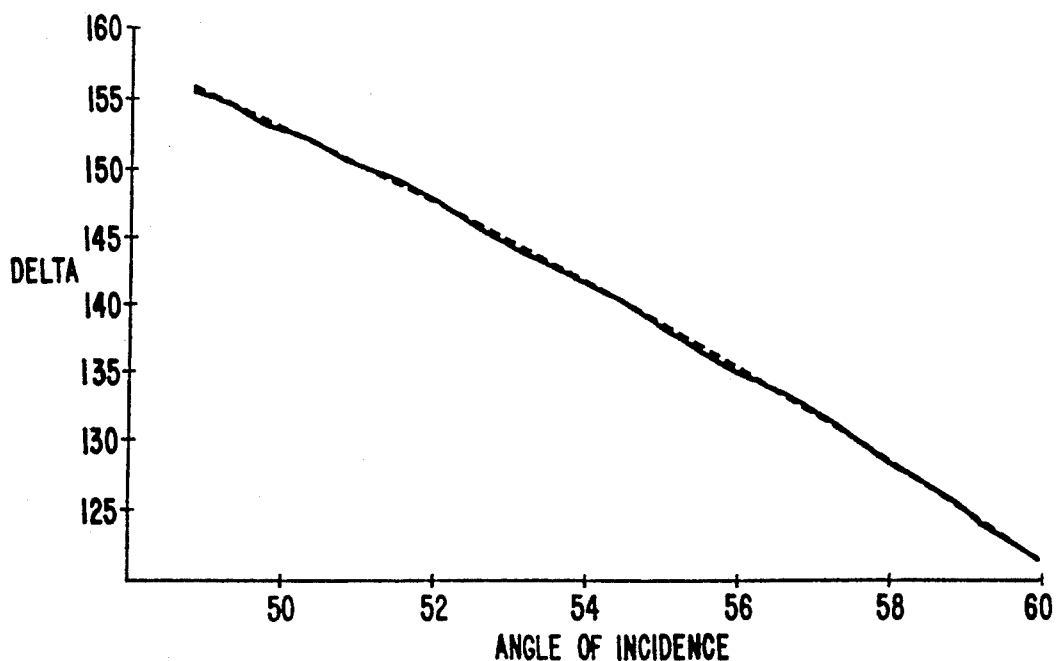
FIG. 7B is a graph of measured values of delta as a function of angle of incidence obtained from a sample using an ellipsometer according to the invention.

FIGS. 7A and 7B show actual ellipsometric data obtained at a plurality of angles of incidence of an instrument designed and constructed according to the preferred embodiment with a range of angles of 10 degrees. These measurements were made on a 1138 Angstrom film of silicon dioxide on a silicon substrate. The solid lines are the measured delta and psi values while the dashed lines represent the theoretical delta and psi computed for this sample.

Figure 4B:
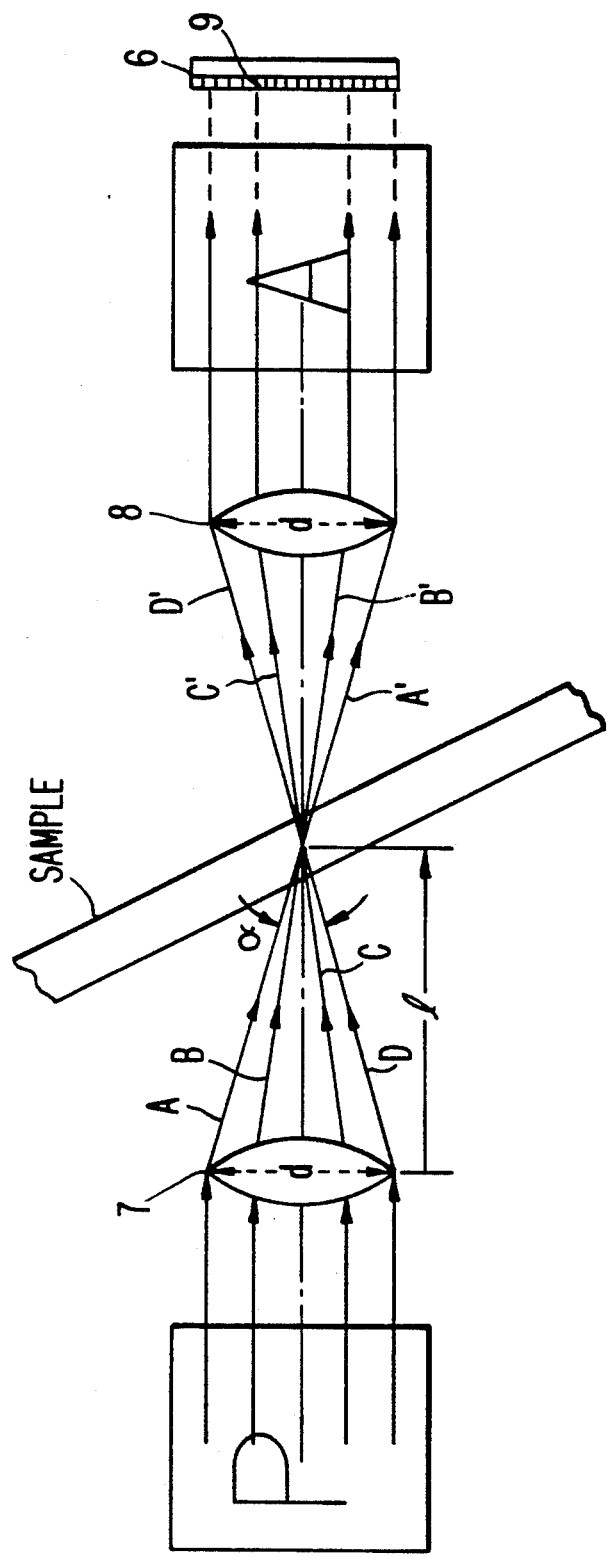
FIG. 4B is the simplified ellipsometer of FIG. 4A but arranged to detect light transmitted through the sample at each of a plurality of angles.

The ellipsometer of FIG. 3B is like that of FIG. 3A except that it has more than one light source, namely an additional, monochromatic light source and also a polychromatic light source as shown in FIG. 3B. The several light sources are arranged to direct light along a common optical axis of the ellipsometer by way of one or more of mirrors, beam combiners and shutters as depicted in the drawing. Alternatively, the light sources could be selectively energized for providing the light from only one of the sources without need for shutters.

While we have shown and described only several embodiments in accordance with the present invention, it is understood that the same is not limited thereto, but is susceptible to numerous changes and modifications as known to those skilled in the art. Therefore, we do not wish to be limited to the details shown and described herein, but intend to cover all such changes and modifications as are encompassed by the scope of the appended claims.

We claim:

1. An ellipsometry method comprising directing polarized light so that it interacts with an optical system under study and measuring the change in polarization state of the light interacted with the optical system, wherein polarized light from a single beam or light is simultaneously directed to interact with the optical system at different angles of incidence and wherein the change in polarization state is measured for each of a plurality of said different angles of incidence.

2. An ellipsometry method according to claim 1, wherein the light is interacted with the optical system under study by transmitting it through a material of the optical system.

3. An ellipsometry method according to claim 1, wherein the light is interacted with from the optical system under study by reflecting it from a surface of the optical system.

4. An ellipsometry method according to claim 1, wherein the light is directed onto a surface of the optical system under study at a single spot with a cone of polarized light derived from a single beam.

5. An ellipsometry method according to claim 1, wherein the angles of incidence vary over a range of angles of at least 1-2 degrees.

6. An ellipsometry method according to claim 5, wherein the range of angles of incidence is from two degrees to more than thirty degrees.

7. An ellipsometry method according to claim 1, wherein the light at different angles of incidence is provided by directing parallel light through at least one lens for focusing the light on the optical system under study, the lens having an effective aperture to focal length ratio for focusing the light on the optical system under study with angles of incidence which vary over a range of at least 1-2 degrees.

8. An ellipsometry method according to claim 1, wherein the light directed for interaction with the optical system under study at different angles of incidence is elliptically polarized light.

9. An ellipsometry method according to claim 1, wherein the polarized light is simultaneously directed at different angles of incidence onto the same spot on a surface of the optical system under study for reflection from the surface.

10. An ellipsometry method according to claim 9, wherein said spot has a diameter of less than or equal to ten microns.

11. An ellipsometry method according to claim 1, wherein the polarized light is monochromatic light.

12. An ellipsometry method according to claim 1, wherein the polarized light comprises two or more quasimonochromatic wavelength regions and all but one of the wavelength regions is excluded at a given time.

13. An ellipsometry method according to claim 1, wherein said step of measuring includes detecting the light interacted with the optical system under study for each of a plurality of different angles of incidence.

14. An ellipsometry method according to claim 13, wherein the interacted light is refocused by passing it through at least one lens before the light is detected.

15. An ellipsometry method according to claim 13, wherein the interacted light for each of a plurality of different angles of incident light is separately detected simultaneously.

16. An ellipsometry method according to claim 13, wherein a plurality of light detector means are provided in an array located so that respective light detector means intercept and detect interacted light from different angles of incident light.

17. An ellipsometry method according to claim 13, further comprising restricting the wavelength regions of the detected light to a quasimonochromatic portion.

18. An ellipsometry method according to claim 13, further comprising the steps of dispersing the light interacted with the optical system under study and detecting wavelength variation and angle of incidence variation of the dispersed light.

19. An ellipsometry method according to claim 18, wherein the polarized light is polychromatic light.

20. An ellipsometry method according to claim 1, including determining a change in amplitude ratio tan $\psi$ and a change in phase difference $\Delta$ for light interacted with the optical system under study for each of said plurality of different angles of incidence.

21. An ellipsometry method according to claim 1, wherein each of said plurality of different angles of incidence is a narrow range of angles of incidence of the interacted light.

22. An ellipsometer comprising means for directing polarized light so that it interacts with an optical system under study, and means for measuring the change in polarization state of said light interacted with the optical system under study, wherein said means for directing polarized light includes means for simultaneously directing polarized light from a single beam of light onto the optical system under study at different angles of incidence, and wherein said means for measuring measures the change in polarization stat of light interacted with the optical system under study for each of a plurality of said different angles of incidence.

23. An ellipsometer according to claim 22, wherein said different angles of incidence vary over a range of at least 1-2 degrees.

24. An ellipsometer according to claim 23, wherein the range of angles of incidence is from two degrees to more than thirty degrees.

25. An ellipsometer according to claim 22, wherein said means for simultaneously directing includes at least one lens for focusing the light on the optical system under study, the at least one lens having an effective aperture to focal length ratio for focusing the light on the optical system under study with angles of incidence which vary over a range of at least 1-2 degrees.

26. An ellipsometer according to claim 22, wherein said means for directing polarized light directs elliptically polarized light onto the optical system under study.

27. An ellipsometer according to claim 22, wherein said means for simultaneously directing polarized light onto the optical system under study at different angles of incidence directs the light at different angles of incidence onto the same spot on optical system under study.

28. An ellipsometer according to claim 22, wherein said polarized light is monochromatic light.

29. An ellipsometer according to claim 22, wherein said means for directing directs polarized light comprising two or more quasimonochromatic wavelength regions, and further comprising means for selectively excluding all but one of the wavelength regions at a time.

30. An ellipsometer according to claim 22, wherein said means for measuring includes a plurality of detectors for detecting the light interacted with the optical system under study at each of a plurality of said different angles of incidence.

31. An ellipsometer according to claim 30, further comprising a lens or lenses for refocusing the interacted light before it is detected by said means for detecting.

32. An ellipsometer according to claim 30, wherein said plurality of detectors is in the form of an array of light detectors located so that respective light detectors intercept and detect interacted light from different angles of incident light.

33. An ellipsometer according to claim 32, wherein said array is a linear array of light detectors.

34. An ellipsometer according to claim 32, wherein said detectors are solid-state photosensitive detectors which are integrated on a semiconductor chip.

35. An ellipsometer according to claim 22, further comprising means for dispersing the interacted light and means for detecting wavelength variation together with angle of incidence variation of the dispersed light.

36. An ellipsometer according to claim 35, wherein the polarized light is polychromatic light.

37. An ellipsometer according to claim 22, wherein the means for directing polarized light comprises a plurality of light sources each arranged to provide light which travels along a common optical axis.

38. An ellipsometer according to claim 37, further comprising means for preventing the polarized light from one or more of the plurality of sources from reaching the means for measuring.

39. An ellipsometer according to claim 38, wherein said means for preventing is one of the group consisting of a shutter, a means for de-energizing said one or more light sources and a blocking filter.

40. An ellipsometer according to claim 22, wherein said means for measuring enables determination of a change in amplitude ration tan $\psi$ and a change in phase difference $\Delta$ for light interacted with the optical system under study for each of said plurality different angles of incidence.

41. An ellipsometer according to claim 22, wherein each of said plurality of different angles of incidence is a narrow range of angles of incidence of the interacted light.

42. A method of aligning a sample for ellipsometry comprising directing polarized light onto a surface of the sample at different angles of incidence form a single beam of light so that said light is reflected onto a detector array for detecting the light reflected from the surface for each of a plurality of different angles of incidence, and including the steps of eliminating light rays within a certain area of the light beam directed onto the sample surface, determining which area of the detector array is not illuminated by reflected light as a result of said eliminating, and making any necessary adjustments in the position of the sample so that a correct area of the detector is not illuminated by reflected light.

* * * * *